United States Patent [19]

Mueller

[11] 4,276,384

[45] Jun. 30, 1981

[54] FERMENTER

[75] Inventor: Felix Mueller, Staefa, Switzerland

[73] Assignee: Chemap A.G., Männedorf, Switzerland

[21] Appl. No.: 58,325

[22] Filed: Jul. 17, 1979

[30] Foreign Application Priority Data

Jul. 19, 1978 [CH] Switzerland .................. 7774/78

[51] Int. Cl.³ ............................................. C12M 1/12
[52] U.S. Cl. .................................. 435/311; 435/312; 435/314; 435/316; 210/433.2; 261/DIG. 75
[58] Field of Search ............... 435/311, 309, 312–316, 435/812, 813, 288; 261/DIG. 75, 36 R, 93; 210/433 M, 220, 23 F, 22, 321 R, 2, 11, 12, 15, 218, 500 M

[56] References Cited

U.S. PATENT DOCUMENTS

| 3,228,877 | 1/1966 | Mahon | 210/22 |
| 3,580,840 | 5/1971 | Uridil | 435/311 |
| 3,720,583 | 3/1973 | Fisher | 435/302 |
| 3,880,755 | 4/1975 | Thomas et al. | 210/433 M |
| 3,977,967 | 8/1976 | Trulson et al. | 210/23 F |
| 4,019,962 | 4/1977 | Allen et al. | 435/315 |
| 4,043,903 | 8/1977 | Dor | 435/316 |
| 4,073,696 | 2/1978 | Müller | 435/316 |

*Primary Examiner*—Benoit Castel
*Attorney, Agent, or Firm*—Michael J. Striker

[57] ABSTRACT

A fermenter for cultivating of microorganisms has a container bounding an inner chamber in which microorganisms are accommodated to be cultivated, and at least one diaphragm filter unit which is introduced into the inner chamber, so that the products of metabolism of the microorganisms are continuously separated and withdrawn, simultaneously with cultivation of the microorganisms and directly in the fermenter. A plurality of the diaphragm filter units may be provided and located in a guiding pipe which is arranged centrally of the container.

12 Claims, 7 Drawing Figures

FERMENTER

BACKGROUND OF THE INVENTION

The present invention relates to a fermenter for cultivating of microorganism. More particularly, it relates to a fermenter for cultivating of microorganisms as well as separating and withdrawing products of metabolism of microorganisms.

Products of metabolism of microorganisms are generally separated after the fermentation for extraction of vinegar, wine and antibiotics. This separation is performed by filtration through filters, with the utilization of auxiliary filtering aids in alluvial filters or application or precoating layers over drim rotary filters. Such filtration can take place only in a batch process. At the same time, the above-mentioned products of metabolism are discontinuously processed during the fermentation.

It has been proposed to utilize ultrafiltration for separation of products of fermentation, as disclosed, for example, in Michaels "Ultrafiltration", Booklet No. 905, AMICON Corp., March 1968, p. 22. The U.S. Pat. No. 3,720,583 teaches continuous separation of glucose from an enzymatic hydrolysis with the aid of an ultrafilter which is connected in parallel with an enzyme reactor. In this construction smaller molecules of glucose are separated by diaphragms and larger active enzymes are recirculated.

The known apparatuses have many disadvantages. When the membrane filter is located outside of the reaction container, additional pumps, tubular conduits and armature are necessary. The required pumps have the disadvantage that microorganisms, especially mushrooms, are readily damaged in them. The pumps, as well as measuring probes and pipe section in which they are mounted, are always sources of contamination by external microorganisms. Susceptable microorganisms, such as highly cultivated vinegar bacteriam which cannot tolerate even a short interruption of air supply, must be additionally aerated when they travel from the outlet of the fermenter to a further inlet, so as to maintain the lowest possible level rate of perishing.

SUMMARY OF THE INVENTION

Accordingly, it is an object of the present invention to provide a fermenter for cultivating of microorganisms, which avoids the disadvantages of the prior art.

More particularly it is an object of the present invention to provide a fermenter which has a simple construction and reliably performs the functions of cultivating of microorganisms.

In keeping with these objects and with others which will become apparent hereinafter, one feature of the present invention resides, briefly stated, in a fermenter in which one of several diaphragm filter units are introduced directly in the fermenter, so as to continuously perform separation and withdrawal of products of metabolism of the microorganisms, simultaneously with cultivating of the same and directly in the fermenter.

Such a fermenter has a simple construction and reliably performs its functions. No additional pumps, conduits and armature which otherwise would make the fermenter more complex and be sources of contamination, are needed. The fermenter provides for conditions which are optimum for cultivating of microorganisms and withdrawal of products of their metabolism.

Another feature of the present invention is that the diaphragm filter units may be located in the interior of a guiding pipe accommodated in the inner chamber of the fermenter. The guiding pipe may be arranged centrally of the inner chamber of the fermenter.

Still another feature of the present invention is that the filter units may be formed by permeable pipes, and may have porous diaphragms with pores whose diameter does not exceed 0.2 micrometer.

In accordance with a further feature of the present invention, the diaphragm filter units may extend parallel to a wall of the fermenter. An air supply conduit may be open into each of the diaphragm filter units. It is also possible that each filter unit is mounted rotatable about its longitudinal axis. Each filter unit may be replaceable without interruption of the fermentation process.

The novel features which are considered as characteristic for the invention are set forth in particular in the appended claims. The invention itself, however, both as to its construction and its method of operation, together with additional objects and advantages thereof will be best understood from the following description of specific embodiments when read in connection with the accompanying drawings.

DESCRIPTION OF PREFERRED EMBODIMENTS

Figure 1:
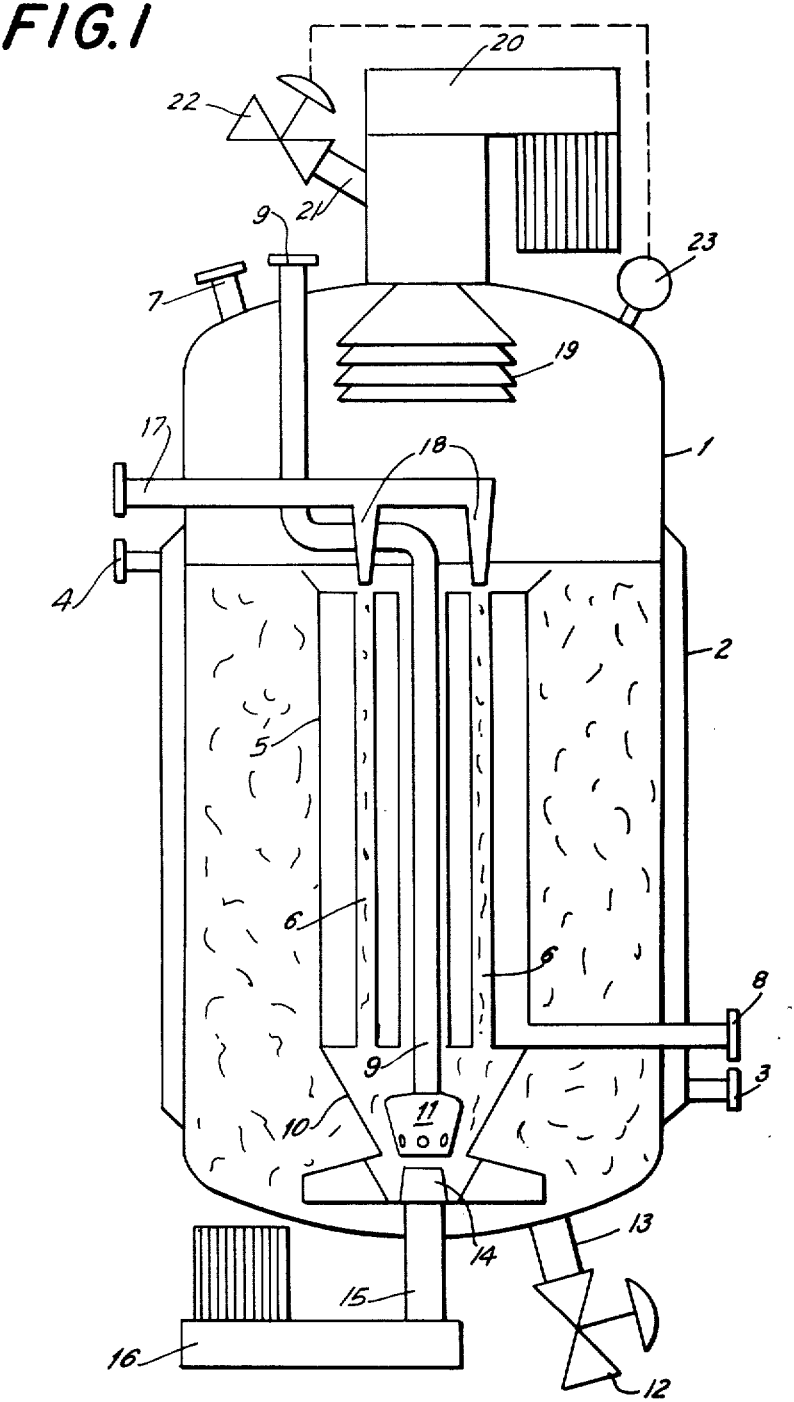
FIG. 1 is a view showing a longitudinal section of a fermenter with filter units mounted therein, in accordance with the present invention.

A fermenter for cultivating microorganisms shown in FIG. 1 has a container 1 with a double circumferential wall 2 and conduits 3 and 4 for supplying and withdrawing, respectively, of heating medium or cooling medium. A guiding pipe 5 is located in the interior of the container 1, advantageously centrally of the latter. A bundle of diaphragm filtering pipes 6 are accommodated in the interior of the guiding pipe 5. P Intermediate spaces 6' between the diaphragm filterng pipes 6 serve for admitting of a permeate, or, in other words, a filtrate or an ultrafiltrate. The intermediate spaces 6' have a single outlet formed by a collecting pipe 8 which extends through the wall of the container 1. A substrate is supplied through a conduit 7 in the top of the fermenter. A main aerating pipe 9 is located in the central region of the guiding pipe 5 and extends into a conical portion 10 of the latter. The main aerating pipe 9 terminates in a distributing member 11. A discharge valve 12 is located below a short pipe 13 arranged in the bottom of the container 1. A rotary turbine 14 is provided which is driven in rotation by an electric motor 16 through a shaft 15.

A further air supply conduit 17 is arranged in an upper part of the container 1. The air supply conduit 17 has branching off portions 18 which are open into the diaphragm filtering pipes 6. Each diaphragm filtering pipe is provided with one branching off air supply portion 18. A mechanical foam-breaking device 19 is mounted in the upper portion of the container 1. It is driven by an electric motor 20 and provided with an exhaust pipe 21. A control valve 22 is connected with the fermenter through a manometer 23 in order to throttle the exhaust gas and to increase the pressure in the inner chamber of the container 1.

Figure 2:
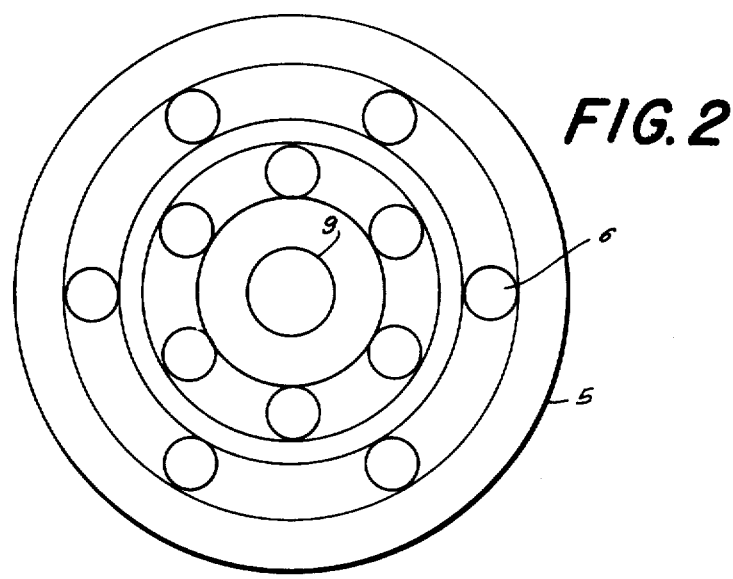
FIG. 2 is a view showing a cross section of a central part of the fermenter of FIG. 1.
Figure 5:
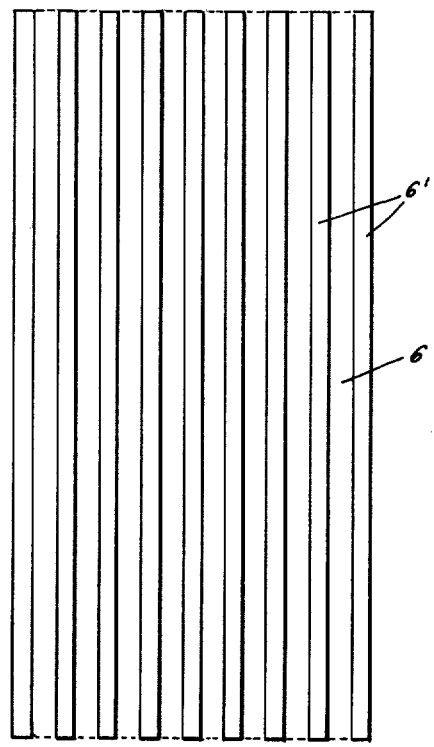
FIG. 5 is a view showing a bundle of the diaphragm filtering pipes.

FIG. 5 shows a bundle of the diaphragm filtering pipes 6 with the intermediate spaces 6' therebetween. FIG. 2 shows the cross section of the diaphragm filtering pipes 6 and the guiding pipe 5 surrounding the same. These Figures do not require additional explanation.

Figure 3:
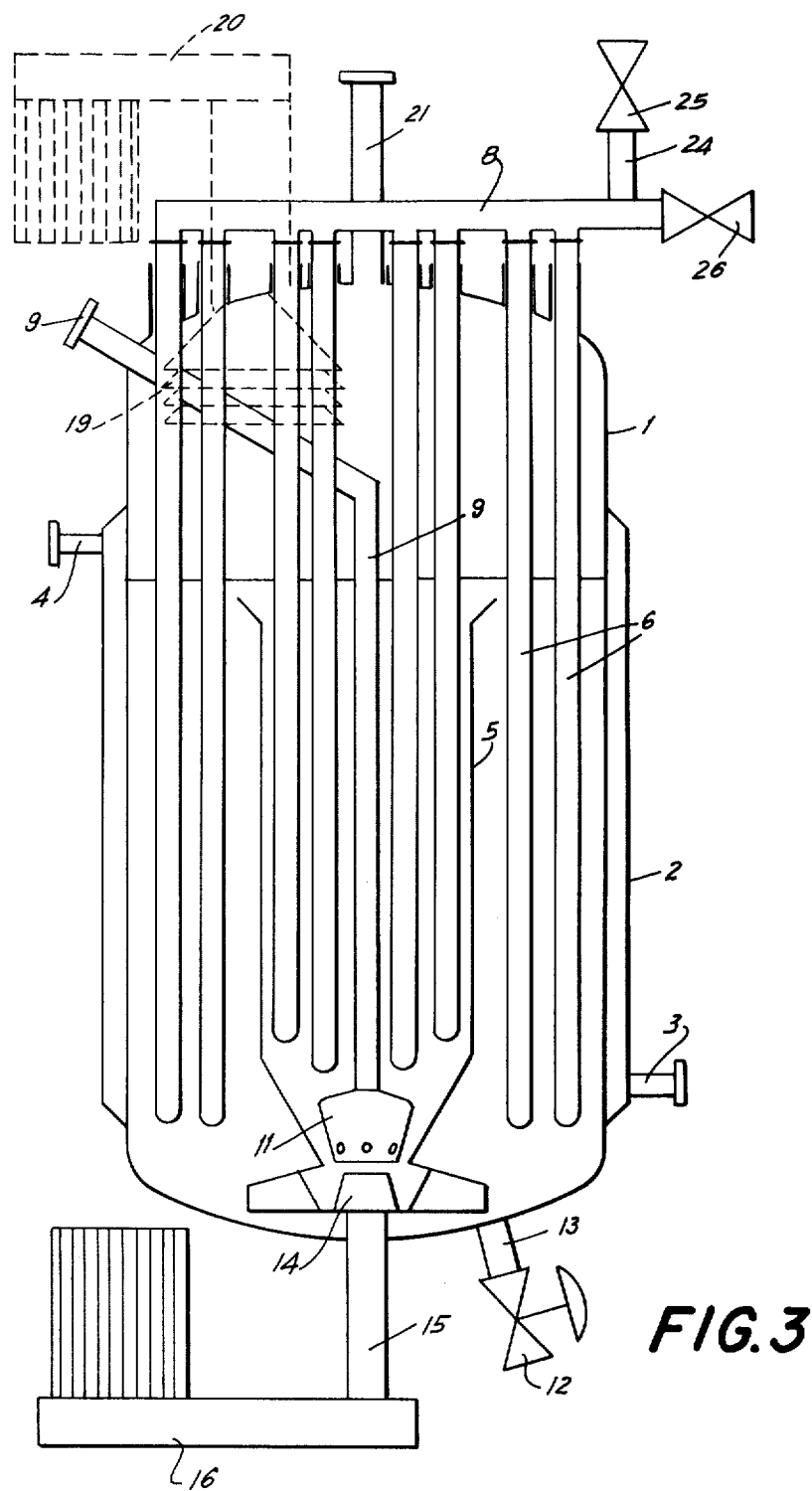
FIG. 3 is a view showing a longitudinal section of a fermenter in accordance with a further embodiment of the present invention.

FIG. 3 shows a fermenter in which the inner chamber bounded by the container 1 is filled by the diaphragm filtering pipes 6 to a greater extent. In addition to the diaphragm filtering pipes 6 located in the interior of the guiding pipe 5, further diaphragm filtering pipes are provided in the space between the guiding pipe 5 and the wall of the container 1. The diaphragm filter units extend upwardly beyond the top of the container 1 and are open into the collecting pipe 8 in the region above the top. The collecting pipe 8 is provided with a short pipe 24 and a valve 25 through which the diaphragm filters can be cleaned by flushing back. During the process of flushing back, an additional valve 26 is closed.

Figure 4:
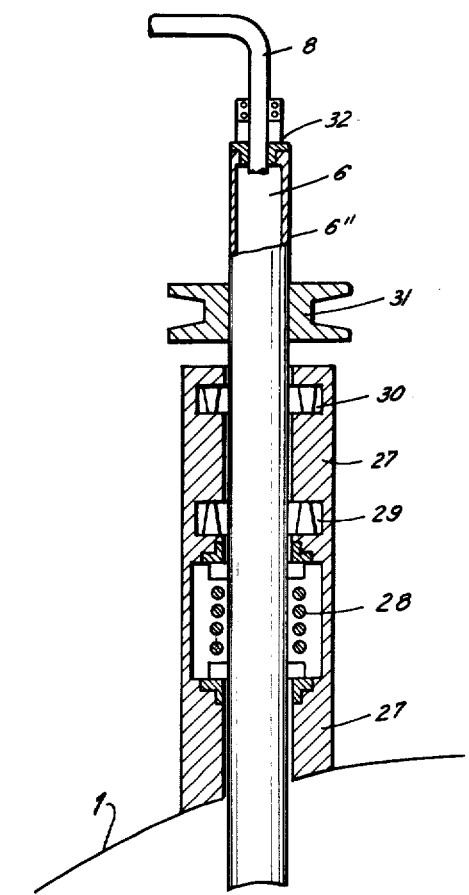
FIG. 4 is a view showing a diaphragm filter unit located outside of the fermenter and partially introduced in the interior of the latter.

FIG. 4 shows a drive part of a rotatable diaphragm filter unit 6 with a diaphragm 6", which is guided in a housing 27. Sealing of the diaphragm filter unit is performed by a two-stage axial slide ring packing 28. The diaphragm filter unit is supported by an upper ball bearing 30 and a lower ball bearing 29. The diaphragm filtering unit can be driven in rotation by a not shown drive through a pulley 31.

Figure 6:
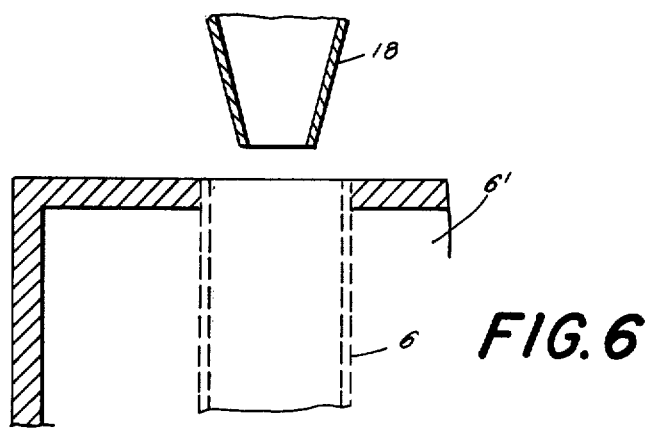
FIG. 6 is a view showing an outlet portion of an air supply conduit and an inlet portion of one of the diaphragm filter pipes, on an enlarged scale.

The diaphragm filter units may be formed as porous pipes whose walls serve as diaphragms and have pores of a diameter not exceeding 0.2 micrometer. As shown in FIG. 6, each diaphragm filter unit may be composed of a porous supporting part and a diaphragm shown by double hatching.

The fermenter in accordance with the present invention operates in the following manner. A substrate is supplied into the container 1 through the conduit 7 under the action of a moderate positive pressure or the aspirating action of the rotary turbine 14 which overcome the predetermined pressure in the interior of the fermenter. The major part of the required aeration air is supplied through the conduit 9 and the distributing member 11 directly to the rotary turbine 14 which is driven by the electric motor 16 through the shaft 15. Simultaneously with the supply of the substrate, plain air or oxygen-containing air is uninterruptedly introduced through the conduit 17 and the portions 18 into the pipes 6 of the diaphragm filters. The nutrient substrate solution which contains microorganisms performing the process of metabolism, is aspirated by the rotary turbine 14, and the air is entrained by the solution in the process of downward movement, whereby sufficient aeration of the solution during this movement is guaranteed. Air bubbles contained in the downward flow are comminuted by the rotary turbine 14 in known manner and, together with the air from the distributing member 11, provide for intensive aeration of the substrate and thereby sufficient air supply to the microorganisms. The diaphragms 6" have a pore diameter which is smaller than the dimension of the smallest microorganisms taking part in the process of metabolism. Thereby, the desired product flows through the diaphragms 6" whereas the microorganisms cannot penetrate through the latter. The permeate is collected in the intermediate spaces 6' of the diaphragm filtering pipes 6 and leave the fermenter through the collecting conduit 8. The fermenter is provided with means for controlling the pressure which includes the above-mentioned contact manometer 23 controlling the valve 22, so that the upper portion of the container 1 is always subjected to a constant positive pressure. Thereby the flow rate of the substrate through the diaphragm filtering pipes is reliably adjusted in order to satisfy the necessary biological requirements. The control valve 22 is mounted in the exhaust conduit 21 of the mechanical foam-breaking device 19 driven by the electric motor 20. It is also possible to provide weight controlling means which is not shown in the drawing and may serve for controlling the relation between recirculated microorganisms and the required optimum concentration. The collecting valve mounted in the short pipe 13 serves the discharge purposes in the case of undesirable increase in the concentration of microorganisms.

The rotatable diaphragm filter makes possible to prevent formation of deposits on the diaphragms 6", with the aid of intermittent rotation of the filters. The diaphragms 6" can also be cleaned by flushing back of the same through the conduit 24, when the valve 25 is open and the valve 24 is closed. The flushing back may also be performed by the permeate during the fermentation process, in required time periods.

Figure 7:
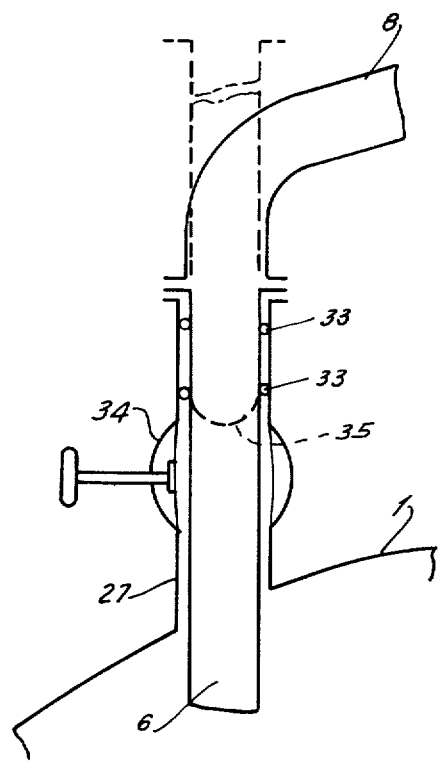
FIG. 7 is a view showing the filtering pipe in detail.

The filtering pipes can be removed during the fermentation. As shown in FIG. 7, the filtering pipe 6 is sealed by two O-rings 33. A ball valve 34 is arranged in the housing 27 and can close the same when the filtering pipe is withdrawn into the position shown in dotted lines. The exchange of the filtering pipes is performed by withdrawing the filtering tube to the above-mentioned position identified by reference numeral 35, closing the housing by the valve 34, and thereafter completely withdrawing the filtering pipe. A new sterile filtering pipe can be inserted into the housing 27 in reverse order.

An especial advantage of the present invention is that the mounting of the diaphragm filter units in the interior of the fermenter guarantees an uninterrupted process of cultivation of microorganisms in sterile condition. In addition to elimination of the damaging action of the above-mentioned pumps, tubular conduits, measuring probes in the case of providing an external system of filtering, no additional expenditures for these structural parts are needed in the inventive fermenter.

A further advantage of the present invention is that it is no longer necessary to provide cooling means of a conventional diaphragm filter system in which the liberated heat must be withdrawn from the required rotary pump of an external diaphragm filter.

A decisive advantage of the inventive fermenter is revealed in the process of fermentation of microorganisms which cannot tolerate shortage of oxygen. Such microorganisms can be effectively cultivated in the inventive fermenter in which the microorganisms, in condition of separation of products of metabolism, can be uninterruptedly supplied with air. As a result of this, microorganisms in all stages of cultivation are not withdrawn from the environment in which they are bred.

Advantageous fields of application of the inventive fermenter is the manufacture of vinegar, alcohol, antibiotics, organic acids, especially citric acid.

It will be understood that each of the elements described above, or two or more together, may also find a useful application in other types of constructions differing from the types described above.

While the invention has been illustrated and described as embodied in a fermenter it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. An improved fermenter for cultivating of microorganisms in a substrate of the type in which a container bounds an inner chamber in which microorganisms are accommodated and cultivated, said improvement comprising substrate inlet means, discharge means and product collecting means for the container, a double circumferential wall for the container having inlet and outlet conduits for supplying and withdrawing of heating or cooling medium through the interior of said double circumferential wall; a guiding pipe located centrally of said container in said inner chamber and having a conical bottom portion; at least one diaphragm filter unit arranged in the interior of said guiding pipe and operative for continuously separating and withdrawing the products of metabolism of the microorganisms, simultaneously with cultivating of the latter directly in the fermenter; a main aerating pipe running from the top of said container through the central region of said guiding pipe and extending into said conical bottom portion of said guiding pipe, said main aerating pipe terminating in a distributing member in said conical bottom portion of said guiding pipe; a rotary turbine beneath said distributing member; and driving means for said rotary turbine, whereby the aspirating action of said rotary turbine provides a moderate pressure overcoming the pressure in the interior of the fermenter and whereby air is entrained by the substrate solution in the process of downward movement and whereby air bubbles of said entrained air are comminuted by said rotary turbine, thereby ensuring sufficient air supply for the microorganisms.

2. A fermenter as defined in claim 1, wherein a plurality of such diaphragm filter units are located in said inner chamber of said container.

3. A fermenter as defined in claim 2, wherein each of said diaphragm filter units is formed as a filtering tube.

4. A fermenter as defined in claim 3, wherein each of said filtering tubes has a porous diaphragm with a plurality of pores each having a diameter which does not exceed 0.01 micrometer.

5. A fermenter as defined in claim 4, wherein said container has a circumferential wall, said diaphragm filter units being distributed over said inner chamber and extending substantially parallel to said circumferential wall of said container.

6. A fermenter as defined in claim 3; and further comprising a plurality of air supply pipes each of which is open into a respective one of said filtering tubes.

7. A fermenter as defined in claim 6; and further comprising an air supply conduit extending into said inner chamber of said container, said air supply pipes branching off from said main air supply conduit.

8. A fermenter as defined in claim 3; and further comprising a collecting conduit communicating with said diaphragm filter units and operative for collecting a permeate, said collecting conduit being provided with a connecting line for flushing back said diaphragm filter units.

9. A fermenter as defined in claim 2, wherein each of said diaphragm filter units has a longitudinal axis and is rotatable about said longitudinal axis.

10. A fermenter as defined in claim 2, wherein said diaphragm filter units are replaceable without interruption of the cultivating process.

11. A fermenter as defined in claim 1; and further comprising an exhaust conduit in said container and provided with a control valve operative for controlling pressure in said inner chamber.

12. A fermenter as defined in claim 11; and further comprising a foam breaking unit located in said container and provided with said exhaust conduit.

* * * * *